United States Patent [19]

Vartiak et al.

[11] 4,123,249

[45] * Oct. 31, 1978

[54] AQUATIC HERBICIDES

[75] Inventors: Joseph F. Vartiak, Naperville, Ill.; George E. Wortley, Jr., Longwood, Fla.

[73] Assignee: Nalco Chemical Company, Oak Brook, Ill.

[ * ] Notice: The portion of the term of this patent subsequent to Feb. 28, 1994, has been disclaimed.

[21] Appl. No.: 825,796

[22] Filed: Aug. 18, 1977

[51] Int. Cl.$^2$ ............................................. A01N 17/00
[52] U.S. Cl. .................................... 71/66; 71/DIG. 1
[58] Field of Search .............................. 71/66, DIG. 1

[56] References Cited

U.S. PATENT DOCUMENTS

| | | | |
|---|---|---|---|
| 3,360,356 | 12/1967 | Vartiak | 71/65 |
| 3,393,990 | 7/1968 | Geary | 71/65 |
| 3,959,237 | 5/1976 | Blank | 71/93 |

FOREIGN PATENT DOCUMENTS 4,810,535  4/1973  Japan .................................. 71/DIG. 1

OTHER PUBLICATIONS

British Pat. 1,056,887, Chem. Abst. vol. 66, (1967) 94152 p.

Primary Examiner—Catherine L. Mills
Attorney, Agent, or Firm—John G. Premo; Robert A. Miller

[57] ABSTRACT

Aquatic herbicides of improved activity are afforded by applying them beneath the surface of waters that contain undesirable aquatic vegetation, said application being performed in the presence of a water-soluble vinyl addition polymer having a molecular weight of at least 10,000, and an inorganic salt cross linking agent.

7 Claims, No Drawings

AQUATIC HERBICIDES

INTRODUCTION

Many species of undesirable aquatic vegetation may be contained or controlled by treating this vegetation with a variety of aquatic herbicides. These herbicides are oftentimes applied by spraying them beneath the water's surface. Many of these aquatic herbicides are applied in conjunction with weighting agents such as sugar or as water-in-oil emulsions which are formulated so that the emulsion slowly inverts in the water. The emulsion droplets, prior to inverting, slowly sink to the bottom of the water where they, hopefully, become affixed to the plant or to the bottom of the body of water where their activity can be focused directly against the vegetation sought to be controlled.

The application of aquatic herbicides as described above could be greatly improved if it were possible to combine with these herbicides either as a neat material or, as they are prepared in commercial formulations, a chemical substance which would allow them to attach themselves selectively to aquatic plants when they are applied under the surface of the water.

THE INVENTION

In accordance with the invention, it has been found that aquatic herbicides may be improved in their activity by applying these herbicides under water to the vegetation to be controlled in the presence of a minor amount of a water-soluble vinyl addition polymer which has a molecular weight of at least 10,000 and an inorganic salt capable of cross linking the water-soluble polymer.

Typical Aquatic Herbicides

While many aquatic herbicides can be improved in their activity by combining them in accordance with the methods of this invention with the water-soluble polymers, certain herbicides are particularly suited for use. Illustrative of such materials are:

7-Oxabicyclo (2,2,1) heptane-2,3dicarboxylic acid;
copper--triethanolamine complex; and
copper-ethylenediamine complex.

The Water-Soluble Polymers

The water-soluble polymers which are useful in this invention have been previously described in numerous publications and patents. The preferred polymers most commonly used in this application are water-soluble polymers and copolymers of acrylic acid and its derivatives. Preferred polymers for use in the practice of this invention include homopolymers of acrylic acid and their water-soluble salts and copolymers of acrylic acid with water-soluble nonionic monomers such as acrylamide. Preferably, these polymers contain from 5–100 weight percent of acrylic acid and from 0–95% by weight of acrylamide or other water-soluble nonionic monomers.

A particularly useful polymer in the above class is a homopolymer of acrylic acid in the sodium salt form. The acrylic acid in the above material may be present in the acid form or may exist as the alkali metal or ammonium salt thereof. It is preferred in the practice of this invention to use sodium polyacrylate. As will be seen from the above description, by the term, "acrylic acid," is also meant other water-soluble materials having a vinyl group and containing a carboxyl group. Examples of monomers of this class include methacrylic acid and α-hydroxyacrylic acid. As stated above, the acrylic acid or its derivatives may be copolymerized with a nonionic vinyl addition monomer, preferably acrylamide, but may also be polymerized with any water-soluble nonionic vinyl addition monomer. These monomers are well known to those skilled in the art and need not be further elaborated on in this specification.

While acrylic acid polymers have been listed above to be the preferred polymeric species in this invention, other various types of water-soluble polymers are known to function in this invention. As a result, we do not wish to be limited to the above compositions but to only those materials which will perform adequately in the course of our invention. For instance, on examining U.S. Pat. Nos. 3,418,237 and 3,259,370 and 3,171,805, it will be seen that the water-soluble vinyl addition polymers may be either cationic or anionic and, in some instances, the ionic charges will be sufficiently slight so that the polymers may be considered as nonionic.

The molecular weight of the polymers described above may vary over a wide range, e.g. 10,000–25,000,000. This invention finds its greatest utility in using acrylic acid polymers which have molecular weights in excess of 10,000 and, most preferably, in excess of 1 million.

Many of these polymers are in the form of dry, granular materials and can be prepared as dilute aqueous solutions, e.g. 1–2%. A convenient form of these polymers are polymers of the type described in U.S. Pat. No. 3,624,019 which is hereinafter incorporated by reference. This patent discloses that when polymers of the above type are in the form of water-in-oil emulsions, they are capable of being added to water and, under certain conditions, are readily inverted to produce dilute solutions of these polymers in very short periods of time. Thus, it is preferred in this invention for ease of handling and dissolution into polymer that the polymer be contained in a water-in-oil emulsion which can be inverted to cause the solubilization of the polymer when contacted with water. Since oil is the continuous phase of these emulsions, it renders them compatible with herbicides which are normally applied or shipped as oil solutions or suspensions.

The Inorganic Crosslinking Agent

In combination with the water-soluble anionic polymer is used an inorganic cation capable of crosslinking the anionic polymer. In utilizing the crosslinkers, they can be added either to the water-in-oil emulsion of the water-soluble anionic polymer or can be added to an aqueous solution of the polymer in the presence of the herbicide. The inorganic crosslinking agents generally employed in this invention are water-soluble trivalent salts of aluminum ($Al^{+3}$), such as aluminum chloride, sodium aluminate, aluminum nitrate, and aluminum phosphate. The preferred inorganic salts for the purpose of our invention are aluminum chloride and sodium aluminate. The inorganic crosslinking agents as seen above are generally added as water-soluble salts and are further added as aqueous solutions to either the polymeric latex or the aqueous solution containing the polymer and herbicide. Since aqueous solutions of these inorganic salts are well known, a detailed description of their preparation is not warranted in this specification.

While the above materials as described all contain aluminum, it is speculated that other inorganic water-soluble cations which are trivalent will also perform adequately in this invention.

The use of the water-soluble inorganic crosslinking agent and its application will depend to a great extent on the characteristics of the herbicide and polymer employed. Aluminum chloride can be added to small quantities of a water-in-oil emulsion of a nonionic polymer such as polyacrylamide, and this water-in-oil emulsion can be added to the water-in-oil emulsions of the anionic polymer allowing for its incorporation into the concentrate. This cannot be done with sodium aluminate since its alkalinity causes hydrolysis of the polymer and instability of the resultant emulsions. This is shown in U.S. Pat. Nos. 3,755,259 and 3,799,902, both of which are hereinafter incorporated by reference. Rather than incorporating the inorganic water-soluble crosslinking agent to the water-in-oil emulsion itself, it can also be added to dilute solutions of the water-soluble polymer after the latices have been inverted with the aquatic herbicide being present. We have found this is a generally satisfactory technique for the application of this invention.

Utilizing the Water-Soluble Polymers and Crosslinking Agents With the Aquatic Herbicides The water-soluble anionic polymers in combination with the water-soluble, inorganic crosslinking agent used in the practice of the invention may be employed in conjunction with the aquatic herbicides in a variety of ways. In one of its simplest forms, the aquatic herbicide would be applied below the surface of the water through a plurality of injection nozzles. The polymer and crosslinking agent in the form of a concentrated liquid would be metered into the herbicide pump where it is mixed with the herbicide just prior to where the feed line goes into the application nozzles. In another embodiment of the invention, the polymer and crosslinking agents may be compatible with the particular herbicidal formulation used and can be directly admixed therewith. In some instances, it is beneficial if the polymer and crosslinking agent are injected below the surface of the water concurrently with the herbicide.

The polymers and crosslinking agents of the invention when used in accordance with the teachings hereof, particularly when applied under conditions of good agitation, tend to encapsulate the active herbicide, carry it down to the surface of the vegetation and its growth situs, and allow it to be released at a fairly uniform rate, thereby achieving maximum killing or control. Without the use of these polymers and their crosslinking aids, many of the herbicides are sufficiently dissipated after being injected into the water where much of the active ingredient does not contact the vegetation, thereby having little or no effect with respect to the control and irradication of undesirable aquatic vegetation.

The amount of polymer and crosslinking agent used to achieve the result of this invention may be varied. The particular amount of polymer utilized will depend upon the particular polymer used, the molecular weight of the polymer, the mode of application, the particular aquatic herbicide with which it is combined, the nature and quantity of the crosslinking agent employed and, of course, the amount of herbicidal material being sprayed per unit of area. Field tests have shown that fairly good control is achieved when the polymer is applied along with the herbicide in a dosage range of 0.005–0.2 pounds of the water-soluble polymer per gallon of solution sprayed. Preferably, from 0.01–0.1 pounds of polymer per gallon are used and, most preferably, from 0.02–0.075 pounds per gallon of solution are utilized. In the preferred practice of this invention, water-in-oil emulsions of the vinyl addition polymer are utilized. These emulsions are commercially available and generally have polymer concentrations of approximately 10–35% by weight. These materials have been successfully used as the following examples show, at a rate of approximately 1.5 gallons of 30% latex per 100 gallons of spray solution which translates to roughly 0.038 pounds of active polymer per gallon of sprayed solution.

The amount of crosslinking agent employed is variable depending on the molecular weight of the polymer employed, the herbicide being utilized, and the amount of solution being sprayed per area. However, we have found that the crosslinking agent should generally be added at a level of from 0.01 to 5.0% and, preferably, 0.5–20% by weight of the polymer utilized. The level of crosslinking agent to be used can be determined easily with simple experimentation to obtain a polymer solution which will be fluid when sprayed and yet have the desirable characteristics of being thick enough to settle rapidly when applied with the herbicide, allowing the entrapment of the herbicide contained in the solution onto the leaves of the aquatic vegetation which is desired to be controlled.

In order to further illustrate the instant invention, the following examples are presented:

EXAMPLE I

A composition would be formulated as follows:

5.0g of a finely powdered aluminum chloride hexahydrate was slowly blended into 95.0g of a water-in-oil emulsion of a water-soluble polyacrylamide containing 27% by weight polyacrylamide, 42.5% water, 28.4% Isopar M, and 1.76% sorbitan monooleate as an emulsifier. After mixing, the resultant water-in-oil emulsion was stable. 5.0g of the above nonionic acrylamide emulsion was then added to 93.0g of a water-in-oil emulsion of sodium polyacrylate containing approximately 30% sodium polyacrylate, 41:9 water, 21:0 Isopar M, and 1:1 of sorbitan monooleate as a surfactant. The sodium polyacrylate had a molecular weight in excess of 1 million. The emulsion would be agitated yielding a stable water-in-oil emulsion of sodium polyacrylate containing dispersed in the discontinuous phase of the emulsion the water-in-oil emulsion of the nonionic polyacrylamide polymer and aluminum chloride. To the above would be added 2.0g of Triton X-114, an ethoxylated nonyl phenol type surfactant, to render the emulsion capable of inverting when it was contacted with water. This material is labeled Example I.

EXAMPLE II

A polymer was prepared as follows:

A water-in-oil emulsion was prepared containing 65:35 copolymer of acrylamide-sodium polyacrylate. The emulsion containing 47.7% water, 29.8% polymer, 26.05% Isopar M, 1.36% sorbitan monooleate as a surfactant. Additionally, 1.0% Surfonic N-95, an alkyl aryl polyethylene glycol ether, and 1.67% Triton X-114, an ethoxylated nonyl phenol type surfactant, were added to render the emulsion capable of inverting when contacted with water. The polymer had a molecular weight in excess of 1 million. This material was labeled Example II.

EXAMPLE III

A series of one acre applications of aquatic herbicide were made in locations in the Southeastern portion of Florida in lakes, canals and rivers infested with Hydrilla.

Test I

Application to one acre plots were made as follows:

The addition of herbicide-polymer complex, which is the subject of this invention, was made utilizing an air boat equipped with a 100 gallon tank, piston pump, and 5 long hoses in the back of the boat. The hoses were weighed down and extended approximately 15 inches below the water. A portable centrifugal pump was present on the boat and was used to add the polymer to the 100 gallon tank containing the herbicide complex. At this location, the polymer latex described in Example I was applied at a level of 1.5% (volume) or 1.5 gallons per 100 gallons of tank mix. The tank mix contained a total of 100 gallons including 2 gallons of Diquat ® and 4 gallons of Komeen ®. Diquat and Komeen are commercially available aquatic herbicides. The material was sprayed at a rate of 100 gallons per acre through the water which had a temperature of 68° F. and was infested with Hydrilla.

Ten weeks after application, an approximate 80% or more of the plant tissue appeared to be dead or dying. Although small sprouts of regrowth could be seen, a successful kill of the Hydrilla had been obtained.

Test II

Also tested was the material of Example II in much the same manner. Here again, 1.5 gallons of the polymeric latex described was applied along with 0.25% of an aqueous solution of sodium aluminate containing 38.2% sodium aluminate. The herbicidal contents of the large tank was the same as described above. Again, a successful kill with 80% or more of the plant tissue beneath the surface of the water was destroyed by this application.

Controls containing no polymer solution were also applied. Satisfactory kill results were also obtained with these trials although it should be noted that the water level was low and little moving water was noted. The control plots were basically employed in this instance to determine the adverse effect, if any, of the polymer solutions. It should be noted that if the water had been higher and a current had existed, it would be expected that the polymer treated plots would have been superior.

It should be seen on the basis of the above examples that the polymer treatment in combination with various aquatic herbicides yield superior control of aquatic vegetation. This is due to the fact that the polymers containing the crosslinking agents apparently form a network encapsulating the water-soluble herbicides and prevent their drift while holding them against the contacted aquatic vegetation. As discussed above, this invention is applicable to control the Hydrilla which are present in great quantities in many canals and the like in areas such as Southern Florida but, of course, can also be applied to control other aquatic vegetation in rivers, lakes, ponds and streams.

Having thus described our invention, we claim:

1. A process for improving the activity of aquatic herbicides which comprises applying these herbicides under water to the vegetation to be controlled in the presence of:

A. From 0.005 to 0.2 pounds of a water soluble vinyl addition polymer per gallon of herbicidal solution applied, said water soluble vinyl addition polymer being selected from the group consisting of acrylamide-acrylic acid copolymers, acrylamide-methacrylic acid copolymers, polyacrylic acid, and polymethacrylic acid, said polymer further characterized as having a molecular weight of at least 10,000; and B. From 0.01–5% by weight of the polymer of an inorganic cross-linking agent from the group consisting of water-soluble trivalent salts of aluminum.

2. The process of claim 1 wherein the water soluble vinyl addition polymer is sodium polyacrylate.

3. The process of claim 1 wherein the inorganic cross-linking agent is selected from the group consisting of sodium aluminate and aluminum chloride.

4. The process of claim 1 wherein the vegetation is Hydrilla.

5. The process of claim 1 wherein the water soluble vinyl addition polymer is contained in a water-in-oil emulsion which can be inverted to cause the solubilization of the polymer when contacted with water.

6. The process of claim 1 wherein the water-soluble vinyl addition polymer is a copolymer of acrylamide and acrylic acid.

7. The process of claim 1 wherein the water-soluble polymer has a molecular weight of at least 1 million.

* * * * *